(12) United States Patent
Harel et al.

(10) Patent No.: US 9,693,552 B2
(45) Date of Patent: Jul. 4, 2017

(54) COMPOSITIONS AND METHODS FOR TARGET DELIVERING A BIOACTIVE AGENT TO AQUATIC ORGANISMS

(71) Applicant: Advanced BioNutrition Corporation, Columbia, MD (US)

(72) Inventors: Moti Harel, Pikesville, MD (US); Brian Carpenter, Baltimore, MD (US); Pete Schmalz, Landenberg, PA (US)

(73) Assignee: ADVANCED BIONUTRITION CORPORATION, Columbia, MD (US)

( * ) Notice: Subject to any disclaimer, the term of this patent is extended or adjusted under 35 U.S.C. 154(b) by 0 days.

(21) Appl. No.: 14/380,219

(22) PCT Filed: Feb. 21, 2013

(86) PCT No.: PCT/US2013/027095
§ 371 (c)(1),
(2) Date: Aug. 21, 2014

(87) PCT Pub. No.: WO2013/126543
PCT Pub. Date: Aug. 29, 2013

(65) Prior Publication Data
US 2015/0017216 A1    Jan. 15, 2015

Related U.S. Application Data (60) Provisional application No. 61/601,290, filed on Feb. 21, 2012.

(51) Int. Cl.
| | |
|---|---|
| A23K 50/80 | (2016.01) |
| A23K 40/10 | (2016.01) |
| A23K 20/24 | (2016.01) |
| A23K 20/26 | (2016.01) |
| A01N 25/10 | (2006.01) |
| A01N 25/24 | (2006.01) |
| A01N 25/28 | (2006.01) |
| A01N 43/90 | (2006.01) |
| A01N 37/46 | (2006.01) |
| A01N 43/24 | (2006.01) |
| A61K 9/16 | (2006.01) |
| A61K 31/122 | (2006.01) |
| A61K 47/42 | (2017.01) |

(52) U.S. Cl.
CPC ............ *A01N 25/10* (2013.01); *A01N 25/24* (2013.01); *A01N 25/28* (2013.01); *A01N 37/46* (2013.01); *A01N 43/24* (2013.01); *A01N 43/90* (2013.01); *A61K 9/1682* (2013.01); *A61K 31/122* (2013.01); *A61K 47/42* (2013.01)

(58) Field of Classification Search
None
See application file for complete search history.

(56) References Cited

U.S. PATENT DOCUMENTS

| | | | |
|---|---|---|---|
| 2,891,355 A | 6/1959 | Nelson | |
| 3,059,379 A | 10/1962 | Attoe | |
| 3,276,857 A | 10/1966 | Stansbury et al. | |
| 3,336,155 A | 8/1967 | Rowe | |
| 3,851,053 A | 11/1974 | Cardarelli et al. | |
| 3,889,007 A * | 6/1975 | Gunter | A23K 1/003 426/635 |
| 4,019,890 A | 4/1977 | Fujita et al. | |
| 4,239,754 A | 12/1980 | Sache | |
| 4,400,374 A | 8/1983 | Cardarelli | |
| 4,428,457 A | 1/1984 | Fikkers | |
| 4,826,842 A * | 5/1989 | Mehlhorn | A01N 43/64 514/241 |
| 5,674,518 A * | 10/1997 | Fajt | A01N 25/002 424/406 |
| 5,747,416 A | 5/1998 | McArdle | |
| 5,858,384 A | 1/1999 | Levy | |
| 6,194,194 B1 | 2/2001 | Molloy | |
| 2003/0152629 A1* | 8/2003 | Shefer | A23G 1/54 424/484 |
| 2004/0009160 A1 | 1/2004 | Villamar et al. | |
| 2004/0185079 A1 | 9/2004 | Zomer | |
| 2006/0104940 A1* | 5/2006 | Heinrichs | A61K 8/8152 424/78.03 |
| 2006/0258623 A1 | 11/2006 | Harel et al. | |
| 2007/0053956 A1 | 3/2007 | Tandler | |
| 2007/0104866 A1* | 5/2007 | McClements | A23D 7/0053 427/213.3 |
| 2008/0044481 A1* | 2/2008 | Harel | A61K 9/127 424/490 |
| 2011/0180010 A1* | 7/2011 | Guo | A23K 1/1606 119/230 |
| 2011/0293657 A1 | 12/2011 | Harel | |
| 2012/0322663 A1* | 12/2012 | Harel | A61K 9/1623 504/358 |

FOREIGN PATENT DOCUMENTS

| | | |
|---|---|---|
| CN | 1454058 | 11/2003 |
| WO | 0200035 | 1/2002 |
| WO | WO 2005/115341 A2 | 12/2005 |
| WO | 2007034250 | 3/2007 |

OTHER PUBLICATIONS

Chemical Book, webpage at www.chemicalbook.com [retrieved on Dec. 18, 2015]. Retrieved from the Internet: <URL: http://www.chemicalbook.com/ChemicalProductProperty_US_CB9199608.aspx>.*

(Continued)

*Primary Examiner* — Robert T Crow
*Assistant Examiner* — John P Nguyen
(74) *Attorney, Agent, or Firm* — RatnerPrestia (57) ABSTRACT

Biodegradable and nutritionally attractive composition comprising biocidal or antibiotic compounds and/or microbes having bio-adhesion and controlled buoyancy properties are selectively fed to an aquatic organism in open or closed water-bodies, and bioactive components are released upon contact with mucosal tissues such as gill, skin or along the digestive tract of the selected aquatic organism.

30 Claims, 5 Drawing Sheets

(56) References Cited

OTHER PUBLICATIONS

"Material Safety Data Sheet—Calcium phosphate, tribasic, powder, c.p.", Acros Organics, 4 pages, 2009.*

David C. Aldridge et al., "Microencapsulated Biobullets for the Control of Biofouling Zebra Mussels," vol. 40, No. 3, 2006, Environmental Science and Technology, 975-979.

Karen Perry et al., "Detecting Physiological and Pesticide-Induced Apoptosis in Early Developmental Stages of Invasive Bivalves," Hydrobiologia (2009) 628: 153-164.

Daniel P. Molloy et al., "Overview of a Novel Green Technology: Biological Control of Zebra and Quagga Mussels With Pseudomonas Fluorescens," Bacterial Project Overview, pp. 1-9, Aug. 24, 2007.

David C. Sigee, "Freshwater Microbiology: Biodiversity and Dynamic Interactions of Microorganisms in the Aquatic Environment," John Wiley and Sons, Ltd. 2005—524 pages.

D. F. Villamar et al., "Delivery of Dietary Components to Larval Shrimp (*Penaeus vannamei*) by Means of Complex Microcapsules," Marine Biology, 115, 635-642 (1993).

D. Siebers et al., "Amino-Acid Uptake by Mussels, *Mytilus edulis*, From Natural Seawater in a Flow-Through System," Helgoland Marine Search, vol. 38, 189-199 (1984).

"Registration Eligibility Decision for Rotenone" EPA 738-R-07-005, Mar. 2007.

"Registration Eligibility Decision for Antimycin A" EPA 738-R-07-007, May 2005.

International Preliminary Report on Patentability for Application No. PCT/US2013/027095 dated Sep. 4, 2014.

Joseph M. Caffrey et al., "Current Status of Ireland's Newest Invasive Species—The Asian Clam *Corbicula fluminea* (Müller, 1774), " Aquatic Invasions (2011) vol. 6, Issue 3: 291-299.

M. S. Kornis et al., "Twenty Years of Invasion: A Review of Round Goby *Neogobius melanostomus* Biology, Spread and Ecological Implications," Journal of Fish Biology (2012), 80, 235-285.

Richard M. Mack et al., "Biotic Invasions: Causes, Epidemiology, Global Consequences, and Control," Ecological Applications, 10(3), 2000, pp. 689-710.

Judith H. Myers et al., "Eradication Revisited—Dealing With Non-Indigenous Species," Trends in Ecology and Evolution, vol. 15, No. 8, Aug. 2000, pp. 316-320.

Charles R. O'Neill et al., "The Zebra Mussel (*Dreissena polymorpha*): An Unwelcome North American Invader," Coastal Resources Fact Sheet, Nov. 1991, Sea Grant, Cornell Cooperative Extension, State University of New York.

David Pimentel et al., "Environmental and Economic Costs of Non-Indigenous Species in the United States," BioScience vol. 50, No. 1, Jan. 2000, pp. 53-65.

D. Siebers et al., "Amino-Acid Uptake by Mussels, *Mytilus edulis*, From Natural Seawater in a Flow-Through System," Helgoland Marine Search, 1984, vol. 38, Issue 1, pp. 189-199.

Robert W. Varney, "Fighting the Spread of Invasive Species in Connecticut/Vermont," U.S. Environmental Protection Agency (EPA), Jun. 17, 2004, www.epa.gov/libraries/region1.

D. F. Villamar et al., "Delivery of Dietary Components to Larval Shrimp (*Penaeus vannamei*) by Means of Complex Microcapsules," Marine Biology, Apr. 1993, vol. 115, Issue 4, pp. 635-642.

International Search Report for International Application No. PCT/US2013/027095 dated May 15, 2013.

Chinese Office Action mailed Sep. 1, 2015 in Chinese Application No. 201380010302.0, including English language translation.

Extended European Search Report dated Mar. 1, 2016 for EP Application No. 13751930.2.

Australian Examination Report dated Nov. 25, 2015 in Australian Application No. 2013222465.

Chilean Office Action dated Mar. 28, 2016 for Chilean Application No. 2221-14 with translation.

Chilean Office Action for Application No. 2014-002221, dated Sep. 28, 2016, 8 pages.

European Communication for EP Application No. 13751930.2, dated Jan. 20, 2017, 3 pages.

* cited by examiner

COMPOSITIONS AND METHODS FOR TARGET DELIVERING A BIOACTIVE AGENT TO AQUATIC ORGANISMS

This application is the National Phase filing of international patent application number PCT/US2013/027095, filed 21 Feb. 2013, and claims priority of U.S. provisional patent application No. 61/601,290, filed 21 Feb. 2012, the entirety of which applications are incorporated by reference herein for all purposes. This work was supported through a purchase order from the U.S. Department of the Interior, U.S. Geological Survey.

BACKGROUND OF THE INVENTION

Field of the Invention

The invention relates to biodegradable and nutritionally attractive composition comprising biocidal or antibiotic compounds and/or microbes having bio-adhesion and controlled buoyancy properties for selectively fed to an aquatic organism in open or close water-bodies, and bioactive components are released upon contact with mucosal tissues such as gill, skin or along the digestive tract of the selected aquatic organism.

Description of the Related Art

Non-indigenous aquatic species are rapidly spreading worldwide, causing both a severe loss of global biodiversity and environmental and economic damages [1, 2, 3]. In addition to direct effects on habitat quality, the expected climate changes will foster the expansion of invasive species into new areas and magnify the effects already present by altering competitive dominance, increasing predation and infectious diseases. Aquatic species that are considered invasive are non-native species, as they are free from natural predators, reproduce rapidly and aggressively compete with native species. Invasive predatory species prey upon native species and disrupt their aquatic food web. They can affect property values, and influence economies of water-dependent communities.

For example, many non-native aquatic plants, animals and microscopic organisms have been introduced into the Great Lakes since the early 1800s, either accidentally or intentionally. Many of them over-populate the lakes and surrounding rivers. They prey on native fish and plants, and disrupt the ecosystem in the lakes. They also harm the recreational and agricultural activities by damaging boats and gear, underwater cables, oil rig platforms, buoys, fishing nets, clogging water pipes and hydro-power facilities, jamming the fresh water supply chain and choking off irrigation systems in the region. Losses in the U.S. alone are estimated at $78.5 billion annually [4]. Recent efforts across many countries have highlighted the urgent need for more rigorous and comprehensive management programs to prevent and contain the worldwide spread of non-indigenous species.

The invasion of Zebra mussel (*Dreissena polymorpha*) and Asian clam (*Corbicula fluminea*) are of particular concern given their ability to rapidly cover the surface of hard submerged substrates, reduce phytoplankton biomass and hence disturb pelagic food webs and act as major macro fouling species of water intake structures and pipes used in municipal, agricultural, industrial, and power station water systems [5, 6]. Asian clams are found in 36 of the contiguous states of the United States as well as in Hawaii. The zebra mussel, introduced into the U.S. in 1986, has spread rapidly throughout the Great Lakes, St. Lawrence River, and waterways associated with the Mississippi River. It is expected that the mussels will, within 20-25 years, infest most areas south of Central Canada and north of the Florida Panhandle from the Pacific Coast to the Atlantic Coast. As the zebra mussel advances, the prognosis for native freshwater bivalve populations is bleak, especially for those populations of species considered threatened and endangered [7].

Another harmful invader is the round goby *Neogobius melanostomus*, which is one of the most wide-ranging invasive fish on earth. The fish has substantial introduced populations within the Laurentian Great Lakes watershed, the Baltic Sea and several major European rivers. *Neogobius melanostomus* inhabit a wide range of temperate freshwater and brackish-water ecosystems and without establishing rigorous management programs will probably continue to spread via ballast water, accidental bait release and natural dispersal worldwide [8].

There are many methods of controlling the spread of invasive species. These methods include the mechanical removal such as dredging, chain dragging and hand raking, predator removal, and chemical, biochemical and biological control. It is equally important to manage the invasive species in a safe, environmentally responsible and cost effective manner. For example, in order to find less harmful methods to control invasive mussels, New York State Museum's (NYSM) Field Research Laboratory screened more than 700 bacterial isolates as potential biological control agents against zebra and quagga mussels. As a result, they found a highly effective and lethal strain isolate of *Pseudomonas fluorescens* (CL145A) against these mussels (U.S. Pat. No. 6,194,194). This harmless bacterium is present in all North American water bodies and even in the average household kitchen and refrigerator [9].

Application of biocides and toxicants is one of the effective ways to reduce a population of invasive species. However, application techniques have not been perfected and as a result those methods have been quite ineffective in eradicating the invasive organism. Another disadvantage is that many toxicants in use such as sodium hypochlorite, surfactants, ammonium salts, N-triphenylmethyl-morpholine have either low toxicity or non-selectively affect the entire water ecosystems. For example, CLAM-TROL pesticide, produced by Betz Chemicals, H130 didecyldimethylammonium chloride produced by Calgon Corp. and 4-trifluoroethyl-4-nitrophenol marketed as BAYLUSCIDE pesticide (Bayer) are acutely toxic to fish and other aquatic organisms and are believed to be quite persistent in the environment [10]. To date, none of those chemical treatments seems likely to replace simple chlorination as the standard treatment for zebra mussels.

The two most widely used fish toxicants in aquatic systems are Rotenone and antimycin A. Rotenone, is a botanical pesticide registered by the EPA for piscicidal (fish kill) uses. The chemical is related to isoflavonoid compounds derived from the roots of *Derris* spp., *Lonchocarpus* spp., and *Tephrosia* spp., and primarily found in Southeast Asia, South America, and East Africa, respectively. Rotenone products are classified as Restricted Use Pesticides (RUP) due to acute inhalation, acute oral, and aquatic toxicity (see EPA 738-R-07-005, March 2007, Registration Eligibility Decision for Rotenone). Rotenone does not dissolve in water. In order to disperse it in water so that it can be effective at low concentrations, rotenone must be formulated with solvents. There are a couple of commercial liquid emulsion products containing rotenone as the active ingredient that can be used for treating aquatic systems. For example, one product is called Nusyn-Noxfish®, the other CFT Legumine®. These piscicides are usually applied by spraying the emulsion on the surface of the water. However, these emulsion-type piscicidal compositions have many disadvantages, as described below.

Antimycin A is a relatively new fish toxicant, and primarily applied as a single management tool. Over the past decade antimycin A has been used by Federal and state agencies to restore threatened/endangered fish to their native habitats (see EPA 738-R-07-007, May 2005, Registration Eligibility Decision for Antimycin A). Antimycin A is also a Restricted Use Pesticide registered by EPA for piscicidal (fish kill) uses. Derived as a fermentation product from *Streptomyces* mold, the chemical is applied directly to water to renovate recreational fish populations and to remove scaled fish from catfish fingerling and food fish production ponds.

This toxicant is marketed under the trade name of "Fintrol." Currently, there are three registered formulations of antimycin A available. Fintrol-5 consists of antimycin A coated on sand grains in such a way as to release the toxicant evenly in the first 5 feet of water—as the sand sinks; Fintrol-15 which releases it in the first 15 feet of depth, and a liquid, Fintrol Concentrate, which was developed for use in very shallow running waters and streams. Since its introduction, antimycin A has become an attractive pesticide because of its relative specificity to fish, i.e., the minimal concentrations that kill fish are considered harmless to other aquatic life and mammals. It is effective in very small concentrations against all life stages of fish, egg through adult. Its respiratory inhibiting properties are irreversible at lethal dosages, and as importantly, it rapidly degrades in open environment.

Efforts to better control the release of the toxicant are well known, particularly in the agricultural industry. For example, U.S. Pat. Nos. 3,851,053 and 4,400,374 disclose various polymers with extended diffusion path length. Typically, agents incorporated are organic pesticides, and the matrix type is an elastomer such as natural rubber, styrene-butyl styrene rubber, and the like. It is, however, well known in the art that almost all organic and inorganic pesticidal agents lack solubility in those plastic matrices.

Other known encapsulating systems include; U.S. Pat. Nos. 3,059,379 and 4,428,457 in which a core-granulated fertilizer is encapsulated in porous thin film; U.S. Pat. No. 4,019,890 in which granular fertilizers is coated with a water-resisting layer forming a jelly-like gel coating. U.S. Pat. No. 2,891,355 relates to coating foamed polystyrene particles with a solution of fertilizers and nutrients, adding water, and potting a plant therein. Further, Villamar et al. [11] describes the preparation of complex microcapsules (CXMs) consisting of dietary ingredients and lipid-wall microcapsules (LWMs) embedded in particles of a gelled mixture of alginate and gelatin to obtain a single food-particle type used to provide suspension feeders with dietary nutrients. Other fertilizers such as urea can be coated in a granular form as taught in U.S. Pat. No. 3,336,155, thus retarding solution in ground waters. U.S. Pat. No. 3,276,857 teaches that a fertilizer can be encapsulated with asphalt or various waxes and, thus, emission into the environment is slowed. However, none of this prior art discloses a particle wherein the active agent remains within an intact particle even after exposure in water and wherein it is being released only after consumption by an organism. One approach to deliver a toxicant directly to the invasive species is through conventional aquatic feeds in a dry, semi or wet soft form as a pelleted or flaked feed. These feeds however, rapidly deteriorate in water, with physical decomposition and breakdown of the feed starting immediately with feed delivery into the water. Vulnerable bioactive agents started to leach and decompose when the feed become soaked with water, and potentially harming the surrounding endogenous organisms in the ecosystem.

To overcome some of the disadvantages associated with the delivery in dry pelleted feeds, the active agent has been encapsulated within microcapsules. Several types of natural or synthetic polymers have been proposed for use as a matrix for binding and the controlled release of active agents. Examples of such polymers are poly(vinylpyrrolidone), poly (vinylalcohol), poly(ethylene oxide), cellulose and its derivates, silicone and poly(hydroxyethylmethacrylate). Biodegradable matrices are of interest since the degradation of natural polymers like polysaccharides or starches occurs naturally in the aquatic environment. U.S. Pat. No. 4,239,754 describes a system where a nutritional component such as free amino acids, and hormones are entrapped in a liposome and the liposome is further encapsulated in a hydrocolloid matrix. The resulting lipogel microcapsules were either stored as a freeze-dried powder or suspended in water. This type of liposomal membrane or barrier is fragile, potentially expensive and difficult to make and would not likely remain a discrete microcapsule when combined with other materials, or act as an appropriate part of a desirable aquatic invasive species management program.

The encapsulating polymers described in the art do not solve all of the problems associated with delivering the active agent in the aquatic environment. Production of active agents in liposomes and their subsequent encapsulation in a hydrocolloid matrix is a labor-intensive process that adds to the cost of the final product. Drying the microencapsulated active results in oxidation and deactivation of the active component, and more significantly renders the active agent insoluble and thus not bio-available by the organism. Microencapsulated actives that are stored in a dry state still have some of the same disadvantages as described for dry pelleted feeds, as they must still be rehydrated and manually introduced into an aquatic environment. Further, the microencapsulating polymers described in the prior art have not eliminated the decomposition and water leaching problems associated with the use in aquatic environments.

The principle utility of the composition of the present invention lies with its unique controlled buoyancy and bioadhesive matrix, in which the active agent is dispersed in a form of oily droplets. The oil dispersed active agent is enclosed within a particle matrix and will not leach even after extended exposure in water. The bioadhesive polymeric matrix remains intact in the water body wherein mucosal tissues such as gill, skin and digestive tract of the targeted aquatic organism are exploited for uptake and release of the active agent. The method of producing and delivering the composition is economical, environmentally safe and applicable to both freshwater and marine waters. Use of the invention is particularly attractive in controlling major invasive species such as fish, mussel and clam.

SUMMARY OF THE INVENTION

Accordingly, the invention provides a biodegradable and bio-adhesive composition that binds or adheres to mucosal tissues and releases a bioactive agent upon consumption by the aquatic organism and methods for making and targeting delivery of such a composition to an aquatic organism.

In some aspects, the invention provides a biodegradable and bio-adhesive polymer composition, wherein said composition includes natural or synthetic biodegradable polymers and wherein said polymers are biopolymers or modified biopolymers of nucleic acids, amino acids, fatty acids and/or sugar monomers and wherein the synthetic polymers are plastics and/or elastomers.

In some aspects, the invention provides a bio-adhesive polymer composition, as above, wherein said polymer includes poly-cationic or positively charged polymers, such as chitosan and modified chitosan, poly-lysine, poly-ethylenimines (PEI), cationic agar, cationic plastic or latex and polymerizable cationic surfactants and the like.

In some aspects, the invention provides a biodegradable polymeric composition in the form of a dry or wet particulate, macroparticle or a micro-particle wherein an active compound is embedded within the particle polymeric matrix.

In some aspects, the invention provides a composition having a density that is adjustable to achieve neutral or controlled buoyancy in various aquatic environments. In some aspects, the invention provides a composition that remains intact for a desirable period of time upon exposure in water and wherein the embedded active compound is dissolved or dispersed in an organic solvent and will not leach in water. In some aspects, the invention provides a composition wherein the embedded bioactive compound released from the composition upon consumption by the aquatic organism. In some aspects, the invention provides a method for making a biodegradable composition having bioadhesive and adjustable density properties including; Forming a slurry containing a poly-cationic polymer and buoyancy regulating materials; dissolving an active compound in a mixture of water insoluble organic solvents and cationic surfactants; mixing the dissolved active compound in the bio-adhesive polymer slurry; adding attractant nutrient such as fish meal, a protein, a lipid, or a resistant starch to the slurry; pelleting, granulating or atomizing the slurry and hardening the particulate slurry or microdroplets to form solid wet or dry particles in a desirable shape and size distribution.

In some aspects, the invention provides a method for delivering a bioactive agent such as a toxicant, therapeutic or nutraceutical compounds to an organism in aquatic ecosystems including; producing bioadhesive composition containing a bioactive agent; adjusting the size and density of said composition to maximize its availability to the aquatic organism in the targeted water body; dispersing the bioactive particulated composition in an aquatic environment at a sufficient amount to obtain a desired effect on the aquatic organism.

In some aspects of the invention, the bioactive agent is an aquatic biocide or a biological control agent, wherein the agent controls various undesirable vertebrate and invertebrate aquatic organisms such as fish, mussel, clam, sea snail and the like.

In some aspects of the invention, the bioactive agent is a therapeutic agent such as a bactericidal antibiotic or peptide, wherein the therapeutic compound is capable of treating diseased farmed fish.

In some aspects of the invention, the bioactive agent is a nutraceutical agent such as essential fatty acids, carotenes, amino acids, proteins, peptides, hormones and vitamins.

In some aspects of the invention, the polymeric composition contains matrix forming polymers such as alginate, pectin, gelatin, agar, carrageenan, or their modified polymers and a mixture thereof, wherein the bioadhesive polymer such as chitosan, cationic guar and/or other poly-cationic polysaccharides is admixed in.

In some aspects of the invention, the polymeric composition contains matrix forming polymers wherein the matrix forming polymer is the bioadhesive polymer itself such as chitosan, cationic guar and/or other poly-cationic polysaccharides.

In some aspects of the invention, the density of the composition is adjusted by incorporating, in various proportions, water insoluble metal salts or minerals and molten fats, waxes and/or polypropylene wax.

In some aspects of the invention, the composition is pelleted, particulated or atomized into a desired shape and size and hardened by cross-linking salts or chemicals.

In some aspects of the invention, the pelleted or particulated composition is delivered wet or dried in any known drying method including air or vacuum drying and delivered as dry pellets or particulated powder.

In some aspects the invention provides a bio-adhesive composition for releasing an active compound in the digestive tract of an aquatic organism.

In some aspects the invention provides a bio-adhesive composition containing a biocide or a mixture of biocides in the form of wet or dry micro-particle in various size ranges depending on the size preference of the targeted invasive organism. For example, the particle size may be about 5-10 microns for eradicating invasive mussels, such as Zebra mussels, or about 50-150 microns for eradicating invasive fish species, such as Asian carp.

These and other aspects of the present invention will become apparent from the following specification.

BRIEF DESCRIPTION OF THE DRAWINGS

It is to be understood that the disclosed drawings are merely exemplary representative of the invention that may be embodied in various forms. Therefore, specific functional details disclosed herein are not to be interpreted as limiting, but merely as a basis for the claims and as a representative basis for teaching one skilled in the art to variously employ the present invention.

FIG. 1 is a light microscopic view of density-adjusted microparticles containing oil droplets embedded in a matrix of bio-adhesive polymer of the presently claimed invention. The upper picture shows microparticles having their density adjusted for fresh water application, and the lower picture shows microparticles having their density adjusted for marine water application.

FIG. 2 is a view of density-adjusted pellets containing oil droplets embedded in a matrix of alginic acid polymer and bio-adhesive polymer of the presently claimed invention. The left picture shows dry pellets and the right picture shows wet pellets having their density adjusted for sinking in marine water environment.

FIG. 3 demonstrates the controlled buoyancy property (sinking rate in mm/sec) of the composition of the present invention in various water bodies as a function of size and density.

FIG. 4 shows the effect of particle size and density on the sinking rate (mm/sec) in fresh water simulated conditions.

FIG. 5 illustrates that the settling velocity ($V_s$) of the composition of the present invention conforms to Stokes law as depicted from the following equation:

$$V_s=(2/9)((\rho p-\rho f)/\mu)(g*R^2)$$

DETAILED DESCRIPTION OF THE INVENTION

Definitions

In the following description of the invention, it is to be understood that the terms used have their ordinary and accustomed meanings in the art, unless otherwise specified. The term "active agent," "bioactive compound," "Biological control agent," is intended to broadly refer to any toxic, therapeutic or nutraceutical substances capable of treating different forms of living organisms used in fields such as aquatic ecosystems, agriculture and aquaculture. A "Toxic Substance" as defined by the U.S. Environmental Protection Agency (EPA) is "any substance or mixture of substances intended for preventing, destroying, repelling, or mitigating any pest." A toxic agent may be a chemical substance or biological agent (such as a virus or bacteria) used against pests including aquatic invasive organisms, which includes pesticides, piscicides, fungicides, herbicides, insecticides, algaecides and moluscicides. Selective pesticides kill a specific target organism while leaving the desired species relatively unharmed. Nonselective pesticides kill all species with which they come into contact. Suitable aquatic biocides according to the present invention are those registered and regulated by the EPA such as Antimycin A, Piperonyl Butoxide (PBO), Pyrethrins, Rotenone and Cube Resins other than Rotenone, Niclosamide, aminoethanol salt (such as BAYLUSCIDE pesticide), Trifluoromethyl-4-nitrophenol (TFM) and the like. A therapeutic substance tends to overcome disease and promote recovery and includes any antimicrobial substance or drug such as a germicide, antibiotic, antibacterial, antiviral, antifungal, antiprotozoal, antiparasitic and therapeutic proteins and peptides. A nutraceutical substance tends to provide health and medical benefits and includes essential fatty acids such as DHA, EPA and ARA, essential amino acids such as lysine, methionine, arginine and the like, vitamins such as vitamin A, C, D, E and the like, proteins and peptides.

The terms "Aquatic Non-indigenous organism" and "Aquatic Invasive organism or species," are intended to broadly refer to any aquatic organisms that have been introduced into new fresh water or marine ecosystems and are both harming the natural resources in these ecosystems and threatening the human use of these resources. Aquatic invasive organisms according to the present invention would include any species of fish, shellfish, mussel, mollusks, clam and jellyfish.

The term "Biodegradable polymer," is intended to broadly refer to any polymer susceptible to degradation by biological activity, with the degradation accompanied by a lowering of its molar mass.

The term "Cationic or poly-cationic polysaccharide" is intended to broadly refer to any naturally occurring or modified or synthetic cationic polysaccharides, as well as polysaccharides and modified polysaccharide derivatives that have been made cationic by chemical means. This includes, for example, quarternization with various quaternary amine compounds containing reactive chloride or epoxide sites.

The term "Bioadhesive or mucoadhesive polymer" is intended to broadly refer to any suitable cationic polymer that readily bind to negatively charged tissues or organs such as gill or gastric mucosal tissues and transporting bioactive material across cell membranes. Examples of cationic polysaccharides include, but not restricted to, cationic hydroxyethyl cellulose and cationic hydrophobically modified hydroxyethyl cellulose, linear macromolecules such as polyethyleneimine (such as Lupasol® by BASF), poly-L-lysine (PLL) or other poly-cationic amino acids, Chitosan, modified chitosans such as dimethyl, trimethyl and carboxymethyl chitosan, cationic guar and/or other poly-cationic polysaccharides, diethylaminoethyl-dextran (DEAE-dextran), and branched polymers such as poly (amidoamine) (PAMAM) dendrimers and POLECTRON® 430 (by International Specialty Products).

The biodegradable polymeric matrix composition of the invention comprises a polymer susceptible to degradation by biological activity in the aquatic ecosystem. In the broadest aspects of the invention, any natural or synthetic polymer is contemplated to be suitable, including but not limited to, starches and modified cellulose such as ethyl, methyl and carboxymethyl-cellulose and the like; polysaccharides and gums such as agar, carrageenan, alginate, pectin, Chitosan, modified Chitosan, guar gum and the like; proteins such as gelatin, milk proteins, glutens, soy and pea protein isolates, Zein and the like; and molten fats such as saturated or hydrogenated fats, waxes, fatty acid alcohols of longer than 12 carbon chain and paraffin oils. Biodegradation of synthetic polymers can be accomplished by synthesizing the polymers with hydrolytically unstable linkages in the backbone, which is commonly achieved by the use of chemical functional groups such as esters, anhydrides, orthoesters and amides. Most commonly used biodegradable synthetic polymers are poly(glycolic acid) (PGA), poly(lactic acid) (PLA) poly(acrylic acid or methacrylates) and their copolymers, as well as other materials, including poly(dioxanone), poly (trimethylene carbonate) copolymers, and poly(e-caprolactone) homopolymers, polyvinyl pyrrolidone, derivatives of polyvinyl pyrrolidone and copolymers of such.

Generally, a matrix polymer that remains intact in the aquatic environment in the form of a particle for at least several hours is preferred. The backbone polymers of the matrix may essentially be any hydrophilic polymer and preferably such polymers that may be suitable for cross-linking. The preferred matrix polymer is selected from the group consisting of hydrogel polymers and combinations thereof, preferably but not necessarily, cross-linked hydrogel polymers such as alginate, pectin, chitosan, agar, cationic agar, carrageenan, gelatin and combinations thereof. The matrix polymer is preferably used in an amount of between 0.01 and 20% by weight with respect to the total weight of the composition. More preferably, this amount is between 0.05 and 15% by weight with respect to the total weight of the composition and more preferably between 1 and 10% by weight.

The biodegradable polymeric matrix composition of the invention comprises a bioadhesive or mucoadhesive polymer as a delivery vehicle for a bioactive agent. In the broadest aspects of the invention, any cationic or positively charged polymer is contemplated to be suitable, including but not limited to, cationic hydroxyethyl cellulose and cationic hydrophobically modified hydroxyethyl cellulose, polyethyleneimine, diethylaminoethyl-dextran, poly-L-lysine (PLL), chitosan, modified chitosans such as dimethyl, trimethyl and carboxymethyl chitosan, cationic guar and/or other poly-cationic polysaccharides. In a more preferred aspect of the invention, any chitosan and/or modified chitosan are suitable.

In one embodiment of the present invention, the bioadhesive polymer is also serving as the matrix polymer wherein the active agent is embedded in the matrix.

In another embodiment of the present invention, the bioadhesive polymer is added to the matrix polymer to provide adhesive properties to the matrix. The bioadhesive polymer is preferably used in an amount of between 0.01 and 20% by weight with respect to the total weight of the composition. More preferably, this amount is between 0.05 and 15% by weight with respect to the total weight of the composition, and most preferably, between 1 and 10% by weight.

The biodegradable polymeric matrix composition of the invention comprises a mixture of metals or water insoluble salts and natural or synthetic molten fats or waxes in a specific desirable ratio to achieve required particle buoyancy in the targeted aquatic ecosystem. In the broadest aspects of the invention, any water insoluble salt having a density greater than 1 g/cm$^{-3}$, including but not limited to carbonates ($CO_3^{2-}$), phosphates ($PO_4^{2-}$) and sulfates ($SO_4^{2-}$) of Ag, Ba, Ca, Mg and Zn and the like, and any molten fats and natural or synthetic waxes having a density lower than 1 g/cm$^{-3}$, including but not limited to those from plants, insects and animals source, and synthetic waxes that are primarily derived by polymerizing ethylene or alpha olefins are contemplated to be suitable. In a more preferred embodiment of the invention, a mixture of tricalcium phosphate (TCP) and polypropylene wax (PPP) is suitable. The preferred amount of TCP and PPP mixture is between 0.01 and 40% by weight with respect to the total weight of the composition. More preferably, this amount is between 0.05 and 30% by weight with respect to the total weight of the composition. The preferred ratio between the TCP and the PPP is any desirable ratio that is required to achieve the specific particle buoyancy in the targeted aquatic ecosystem. For example, it is to be understood that a composition suitable for treating fresh water ecosystems would contain lower TCP/PPP ratios than a composition suitable for treating marine water ecosystems.

The active compound in the context of the present invention is a biocide, a therapeutic or a nutraceutic substance. A biocide substance is a chemical or a biological control agent, capable of killing, preventing, destroying, repelling, or mitigating various undesirable aquatic organisms such as fish, mussels, clams and the like. In the broadest aspects of the invention, any type of biocide or biological agent (such as a dry toxic virus or bacteria) may be used, including but not limited to pesticides, piscicides, fungicides, herbicides, insecticides, algaecides, moluscicides, and the like. Preferred aquatic biocides according to the present invention are those registered and regulated by the U.S. Environmental Protection Agency (EPA) such as Antimycin A, Piperonyl Butoxide (PBO), Pyrethrins, Rotenone and Cube Resins other than Rotenone, Niclosamide, Aminoethanol salt (such as BAYLUSCIDE pesticide product produced by BASF), Trifluoromethyl-4-nitrophenol (TFM) and the like.

In one embodiment of the present invention, the bioactive substance is a therapeutic agent such as a bactericidal peptide or antibiotic that kills infectious bacteria in targeted aquatic ecosystems or in aquaculture systems. In the broadest aspects of the invention, any type of an antibiotic may be used, including but not limited to germicides, antibacterials, antivirals, antifungals, antiprotozoals and antiparasitics. Specific antibiotic substances includes sulfamides, diaminopyrimidines, penicillins, tetracyclines, cephalosporins, aminoglucosides, chloramphenicol and derivatives, quinolones and fluoroquinolones, nitrofurans, nitroimidazoles and mixtures thereof. In another embodiment of the present invention, the bioactive substance is a nutraceutical compound such as a protein, a peptide, an oil, a vitamin, or a hormone. In the broadest aspects of the invention, any type of a nutraceutical may be used, including but not limited to essential fatty acids such as DHA, EPA and ARA and the like, essential amino acids such as lysine, methionine, arginine and the like, vitamins such as vitamins A, C, D, E and the like, carotenes such as beta carotene, leutene, astaxanthin and the like.

Generally, the bioactive agent is solubilized in an organic solvent before embedding in the polymeric matrix of the present invention. In the broadest aspects of the invention, any type of oil, fat or grease can be used for solubilizing including but not limited to naturally occurring or synthetic oils in either liquid or solid form at ambient temperature. Suitable oil, in the context of the present invention, encompasses all kinds of oil bodies or oil components, in particular, fish oil, vegetable oils like rape seed oil, sunflower oil, soy oil, olive oil, cocoa butter, coconut oil, palm oil, castor oil, and the like, modified vegetable oils like alkoxylated sunflower or soy oil, synthetic (tri) glycerides like technical mixtures of mono, di and triglycerides of C6-C22 fatty acids, and fatty acid alkyl esters like methyl or ethyl esters of vegetable oils. Preferably, the solubility of the bioactive agent in oil is enhanced by the use of surface-active agents such as cationic or nonionic surfactants and most preferably cationic surfactants. Typical non-limiting examples for cationic surfactants are quaternary ammonium salts such as trimethylalkylammonium, chlorides or bromides of benzalkonium and alkylpyridinium ions and amines with amide linkages, polyoxyethylene alkyl and alicyclic amines and the like. The preferred amount of the bioactive agent in the oil is between 0.01 and 10% by weight. More preferably, this amount is the maximal attained solubility of the agent in a given oil/surfactant system. The bioactive/oil solution is preferably used in an amount of between 0.1 and 40% by weight with respect to the total weight of the composition. More preferably, this amount is between 0.5 and 30% by weight with respect to the total weight of the composition and more preferably between 5 and 30% by weight.

In one embodiment of the present invention, the bioactive and oil solution is coated onto carrier particles of a nutrient such as a protein, lipid or starch. In the context of the present invention, these nutrients also serve as nutritional attractants for the targeted aquatic organism to actively consume the composition from the aquatic medium.

In another embodiment of the present invention, the nutrient is preferably taken-up and digested by the targeted aquatic organism. For example, it has been shown that bivalve mussels can, due to their large gill surface areas and the great amounts of water pumped through their mantle cavity, successfully compete with other invertebrates in uptake of certain organic matter such as free amino acids [12, 13]. The inclusion of nutrients in the polymer matrix also provides sites and pores opened by the organism digestive enzymes, which allows the bioactive to be taken up more efficiently. In the broadest aspects of the invention, any type of nutrient can be used including but not limited to amino acids, peptides, enzymes, proteins, protein isolates and meals either from animal or plant source, fatty acids, lipids and starches and their derivatives. Suitable nutrients, in the context of the present invention, encompass all kinds of meals, proteins and free amino acids and starch or a mixture thereof, in particular fishmeal or protein isolates from animal or plant source. The preferred amount of the nutrient in the composition of the invention is between 0.1 and 70% by weight, with respect to the total weight of the composition. More preferably, this amount is between 5 and 60% by weight with respect to the total weight of the composition and more preferably between 10 and 50% by weight.

In accordance with the objectives of the invention, the biodegradable and bioadhesive composition delivery vehicle for an aquatic organism is made, dry or wet, and has a particle size in the range of from about 2 microns to about 10,000 microns. The delivery vehicle is made from a complex of components as disclosed above, including any type of biodegradable polymers such as soluble and resistant starch, gums such as agar, pectin, carrageenan, ethyl, methyl or carboxymethyl cellulose, alginate, wax, fat or protein and a mixture thereof. The gel matrix of the particle is formed by hardening or cross-linking the polymers to provide a stable and intact particle in the aquatic environment. The provided particles are attractive and ingestible by the aquatic organism.

In one embodiment of the preparation method, a solution containing 0.01-10% matrix forming polymer such as alginate or pectin is prepared. A solution containing 0.01-10% bioadhesive polymer such as hydrophobically modified hydroxyethyl cellulose, polyethyleneimine, diethylaminoethyl-dextran, poly-L-lysine (PLL) or chitosan is prepared separately and homogenized with the polymer matrix solution. Buoyancy control compounds containing a mixture of metal salt and hydrophobic wax such as a mixture of TCP and PPP in a desirable ratio is added in an amount between 0.01 and 20% by weight of the polymer solution and homogenized until a smooth slurry is obtained. About 0.1-2% of an emulsifier such as monoglycerides, sorbitan esters, propylene glycol esters, lecithin, polysorbates and sucrose esters of medium and long chain saturated fatty acids can be added to assist with the dispersion of the hydrophobic wax in the slurry.

In an alternative embodiment, the bioadhesive polymer is used to also form the matrix solution, such as a chitosan or cationic agar solution. In one more alternative embodiment, the particle matrix is formed with negatively charged polymers, such as an alginate or pectin followed by a brief soaking of the preformed micro particles in a solution containing positively charged polymer, such as chitosan, PLL or cationic agar, and the like.

In one preferred embodiment, the bioactive substance is solubilized in a mixture of an organic solvent and a cationic surfactant. The preferred organic solvent is any vegetable or animal oil, preferably short carbon chain oils such as oils containing caprylic, capric or lauric acid. Most preferred short carbon chain oil is castor oil. The preferred cationic surfactant is a quaternary ammonium salts surfactant. The bioactive solution is prepared by dissolving the maximal soluble amount of the bioactive in the oil and surfactant system. The bioactive and oil solution can be directly homogenized in the polymer matrix solution in an amount from about 0.01 to about 20% by weight of the polymer solution or coated first on fine particles of a nutrient such as fish meal or soy or pea protein isolate in a ratio of 0.5-1:1 of bioactive and oil mixture: nutrient and then add-mixing the coated nutrient into the polymer matrix solution.

The final slurry is hardened by cross linking or cooling after forming a gel pellet in a desirable size and shape or is atomized using an air, ultrasonic or rotary atomizer, or any other atomizing means known in the art, into a water solution containing 0.1-10% cross-linking compounds such as calcium chloride for cross linking polymers such as pectin or alginate, potassium citrate for cross linking carrageenan based polymers or tripolyphosphate for cross linking chitosan polymers and the likes. The hardened matrix particles are then collected from the cross linking solution and can be packaged wet for application to the aquatic environment in their wet form, or dried by any means known in the art such as air drying, fluidized-bed drying, freeze/vacuum drying, and the like and packaged dry for later use. In an alternative embodiment, the slurry can be spray dried into hot air chamber and the dry particles collected and stored for later use.

In one embodiment of the present invention, the bioactive composition in a desirable size range and density is applied in any fresh, brackish or marine aquatic ecosystem so that, upon contact with water, said composition remains intact in the water for at least several hours and the bioactive is retained within the composition. The composition is then actively consumed and adheres to mucosal tissues of the targeted organism wherein the bioactive compound is released and absorbed by the aquatic organism. In another embodiment, a composition containing a biocide or a mixture of biocides is target-delivered to an undesirable aquatic organism. For example a 1:1 mixture of Rotenone and piperonyl butoxide (PBO) is utilized in the composition of the present invention, in a size range between 5 and 10 microns. The density of the microparticle is adjusted with an appropriate TCP/PPP ratio to slightly above the fresh water density and fresh water bodies are treated with the composition to impede habitats of mussels and sea lamprey species.

In yet another embodiment of the present invention, antimycin A is utilized in the composition of the present invention, and microparticles in a size range between 50 and 100 microns are formed. The density of the microparticles is adjusted with an appropriate TCP and PPP ratio to match the density of aquatic estuaries for control of detrimental or invasive aquatic animal species, such as Asian carp or crayfish.

In still another embodiment of the present invention, the antibiotic oxytetracycline is utilized in the composition of the present invention, and pellets in a size range between 2000 and 5000 microns are formed. The density of the pellets is adjusted with an appropriate TCP/PPP ratio to match the water density of a marine environment, and the pellets used to treat aquatic farmed species, such as a salmonid, against a bacterial infection.

In further embodiment of the present invention, astaxanthin containing—microbial cells or oil extract is utilized in the composition of the present invention, and pellets in a size range between 5000 and 10000 microns are formed. The density of the pellets is adjusted with an appropriate TCP/PPP ratio to match the water density of a marine environment, and the pellets fed to salmon fish about 30 days before harvesting to provide a desirable pigmentation in the fish flesh.

The present invention is further illustrated by the following non-limiting examples.

EXAMPLES

Example 1

Production of Bioadhesive Composition Containing Rotenone for Fresh Water Application In a 40 L stainless steel vessel, 16 L of distilled water was added. Sodium alginate (about 200 g, Manugel® DMB, FMC Biopolymer, Philadelphia, Pa.) was slowly added to the distilled water in the stainless steel tank under a vigorous mixing (2,000 RPM, RS-02, Admix, Manchester, N.H.) until completely dissolved. Liquid soy lecithin (about 120 g, Archer-Daniels-Midland Co., Decatur, Ill.) and TWEEN 80 polyoxyethylene (20) sorbitan monooleate (about 120 g, Sigma) were added to the alginate solution and the solution continued to emulsify for 15 minutes under vigorous mixing (2,000 RPM). Polypropylene wax (about 1000 g, Propylmatte-31, Micro Powders, Inc., Tarrytown, N.Y.) was added to the alginate solution and the solution continued to emulsify for additional 15 minutes under vigorous mixing. The pH of the slurry was then adjusted to 6.2 with 1M glacial acetic acid.

In a separate small 10 L stainless steel vessel, 4 L of distilled water was added and warmed to 50° C. Chitosan (about 120 g, high viscosity chitosan 90% DA, MayPro, Purchase, N.Y.) was slowly added to the warmed water. Chitosan, which is the structural element in the exoskeleton of crustaceans (crabs, shrimp, etc.) is bioadhesive and readily binds to negatively charged entities. It is a linear cationic polysaccharide composed of randomly distributed β-(1-4)-linked D-glucosamine (deacetylated unit) and N-acetyl-D-glucosamine (acetylated unit). Chitosan, is produced commercially by deacetylation of chitin (can be produced from chitin also). The degree of deacetylation (% DA) in commercial chitosans is in the range 60-100%. One hundred fifty (150) g of glacial acetic acid was carefully added (with mixing) to the warm water under a vigorous mixing (2,000 RPM) until the chitosan completely dissolved. The chitosan solution was cooled to room temperature and the pH adjusted to 6.2 with 50% sodium hydroxide solution. The chitosan solution was then combined with the alginate solution under vigorous mixing.

In a one (1) L glass beaker in a fume hood, 20 g of Rotenone (analytical grade, Sigma) was added and dissolved in an equal amount of chloroform. Optionally, the toxicity of the Rotenone can be further enhanced by adding 20 g piperonyl butoxide (PBO, Sigma) with the Rotenone. About two hundred (200) g castor oil (Sigma), 20 g cationic surfactant (Cationic Emulsifier-1, Abitec Corp., Janesville, Wis.) and about 200 g olive oil (available from a local store) were added and mixed together to obtain a clear oily solution. The beaker containing the dissolved Rotenone was placed in 40° C. water bath in the hood and under a stream of nitrogen for about two (2) hours to allow the chloroform to evaporate. The dissolved Rotenone was then slowly mixed with about 1880 g soy protein hydrolyzate (Solae™, Solae LLC, St. Louis, Mo.) until the powder appeared uniformly wet. The Rotenone coated soy protein then slowly added into the alginate/chitosan slurry and gently mixed (500-1000 RPM) until smooth slurry was obtained. Alternatively, the soy protein powder can be mixed separately in the alginate/chitosan slurry followed by mixing in the oil solubilized Rotenone.

Microparticles formation: The Rotenone containing slurry was atomized (Air atomizer ¼ JAU-SS, Spraying Systems Co., Wheaton, Ill.) under 25 psi air pressure and microparticles formed by cross linking in a water bath containing 2% calcium chloride. Microparticles in a size range between 50 microns and 150 microns were screen sieved were evenly spread on a tray at a loading capacity of 1000 g/sq ft and placed on a shelf in a freeze dryer (Model 25 SRC, Virtis, Gardiner, N.Y.). Vacuum pressure was then applied at 100 mTORR and shelf temperature raised to +40° C. Drying was completed within 24 hours. Alternatively, the wet microparticles can be dried in a vacuum dryer or fluidized bed dryer. The composition of the microparticles is provided in Table 1, below.

TABLE 1

| Rotenone microparticle composition (g dry weight/100 g) | |
| --- | --- |
| Alginate | 6 g |
| Chitosan | 3 g |

TABLE 1-continued

| Rotenone microparticle composition (g dry weight/100 g) | |
| --- | --- |
| Soy lecithin | 3 g |
| Tween-80 | 3 g |
| Propylmatte-31 | 26 g |
| Soy protein | 48 g |
| Castor oil | 5 g |
| Olive oil | 5 g |
| Cationic emulsifier | 0.5 g |
| Rotenone 99% crystalline | 0.5 g |

Figure 1:
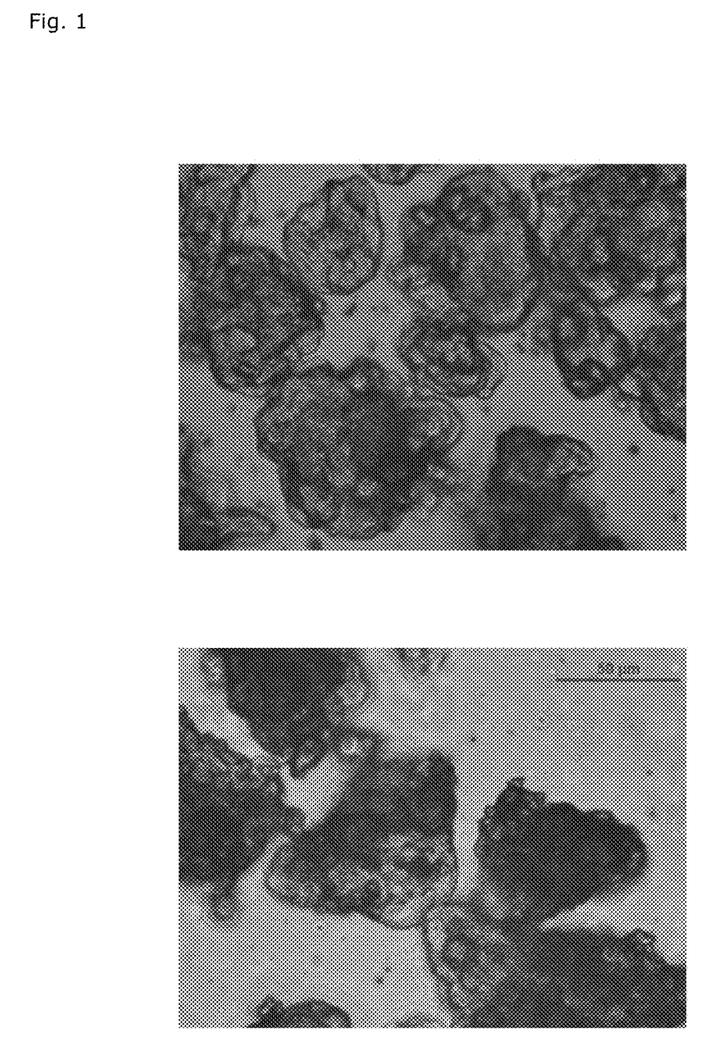
Figure 2:
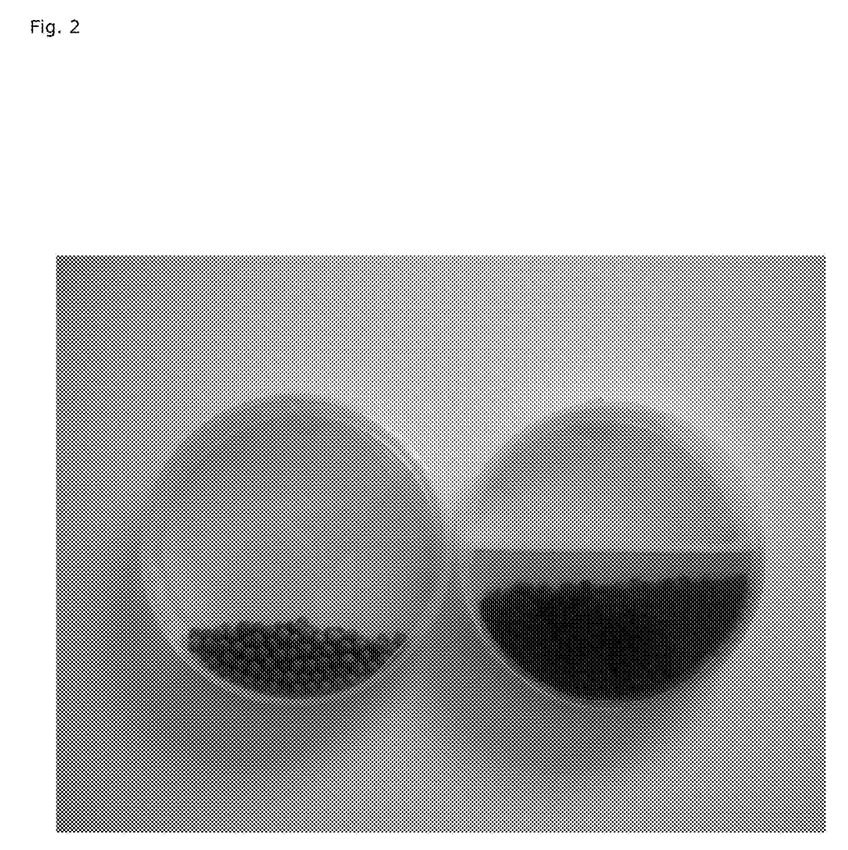

FIG. 1 depicts a light microscope image of the mucoadhesive microparticles of the present invention having adjusted density for fresh water (upper picture) or marine water (lower picture) applications. The Rotenone or Rotenone/PBO microparticles are useful, in accordance with local and federal regulations and registration requirements, for preventing both aquatic invertebrate and vertebrate invasive organisms.

Example 2

Production of Bioadhesive Microparticles Containing Antimycin A for Fresh Water Application In a 20 L stainless steel vessel, 10 L of distilled water was added and warmed to 50° C. Chitosan (about 300 g, high viscosity chitosan 90% DA, MayPro, Purchase, N.Y.) was slowly added to the warmed water. Three hundred (300) g of glacial acetic acid was carefully added (with mixing) to the warm water under a vigorous mixing (2,000 RPM) until the chitosan completely dissolved. The chitosan solution was cooled to room temperature and the pH adjusted to 6.2 with 50% sodium hydroxide solution. Liquid soy lecithin (about 60 g, Archer-Daniels-Midland Co., Decatur, Ill.) and TWEEN 80 polyoxyethylene (20) sorbitan monooleate (about 60 g, Sigma) were added to the alginate solution and the solution continued to emulsify for 15 minutes under vigorous mixing (2,000 RPM). Polypropylene wax (about 500 g, Propylmatte-31, Micro Powders, Inc., Tarrytown, N.Y.) was added to the alginate solution, prepared according to method described under Example 1, and the slurry continued to emulsify for additional 15 minutes under vigorous mixing.

In 1 L glass beaker in a fume hood, 10 g of antimycin A (analytical grade, Sigma) was added and dissolved in an equal amount of chloroform. About one hundred (100) g castor oil (Sigma), 10 g cationic surfactant (Cationic Emulsifier-1, Abitec Corp., Janesville, Wis.) and about 100 g fish oil (available from a local vitamin store) were added and mixed together to obtain a clear oily solution. The beaker containing the dissolved antimycin A was placed in 40° C. water bath in the hood and under a stream of nitrogen for about two (2) hours to allow the chloroform to evaporate. The dissolved antimycin A was then slowly mixed with about 940 g soy protein hydrolyzate (Solae™, Solae LLC, St. Louis, Mo.) until the powder appeared uniformly wet. The antimycin A coated soy protein then slowly added in the chitosan slurry and gently mixed (500-1000 RPM) until a smooth slurry was obtained. Alternatively, the soy protein powder can be mixed separately in the chitosan slurry followed by mixing in the oil solubilized antimycin A.

Microparticles formation: The antimycin A containing slurry was slowly poured on a rotating spinning disc (Southwest Research Institute (SwRI®), San Antonio, Tex.) to form narrow size distribution of microdroplets between 50 microns and 100 microns. Hardened matrix microparticles were formed by cross-linking the chitosan polymers in a water bath containing 10% iso-propanol (70% purity) and 10% tripolyphosphate. Microparticles were harvested from the cross linking bath after a hardening period of about two (2) hours and dried in a fluidized bed dryer (Fluid Bed System model 0002, Fluid Air, Aurora, Ill.). The composition of the microparticles is provided in Table 2. The antimycin A micro particles are useful, in accordance with local and federal regulations and registration requirements, to restore threatened/endangered fish to their native habitat (selective kill) and for disease treatment of farmed fish.

TABLE 2

| Antimycin A microparticle composition (g dry weight/100 g) | |
|---|---|
| Chitosan | 14 g |
| Soy lecithin | 3 g |
| Tween-80 | 3 g |
| Propylmatte-31 | 25 g |
| Soy protein | 44 g |
| Castor oil | 5 g |
| Fish oil | 5 g |
| Cationic emulsifier | 0.5 g |
| Antimycin A | 0.5 g |

Example 3

Production of Bioadhesive Microparticles Containing an Antibiotic for Treating Infected Farmed Fish In a 40 L stainless steel vessel, 16 L of distilled water was added. Sodium alginate (about 200 g, Manugel DMB, FMC Biopolymer, Philadelphia, Pa.) was slowly added to the distilled water in the stainless steel tank under a vigorous mixing (2,000 RPM, RS-02, Admix, Manchester, N.H.) until completely dissolved. Liquid soy lecithin (about 120 g, Archer-Daniels-Midland Co., Decatur, Ill.) and TWEEN 80 polyoxyethylene (20) sorbitan monooleate (about 120 g, Sigma) were added to the alginate solution and the solution continued to emulsify for 15 minutes under vigorous mixing (2,000 RPM). A buoyancy control mixture of tricalcium-phosphate (TCP, technical grade) and Polypropylene wax (TPP, Propylmatte-31, Micro Powders, Inc., Tarrytown, N.Y.) containing 330 g TCP and 260 g TPP was added to the alginate solution and the slurry continued to emulsified for additional 15 minutes under vigorous mixing. The pH of the slurry was then adjusted to 6.2 with 1M glacial acetic acid.

In a separate small 10 L stainless steel vessel, 4 L of distilled water was added and warmed to 50° C. Chitosan (about 120 g, high viscosity chitosan 90% DA, MayPro, Purchase, N.Y.) was slowly added to the warmed water. One hundred fifty (150) g of glacial acetic acid was carefully added (with mixing) to the warm water containing chitosan under vigorous mixing (2,000 RPM) until the chitosan completely dissolved. The chitosan solution was cooled to room temperature and the pH adjusted to 6.2 with 50% sodium hydroxide solution. The chitosan solution was then combined with the alginate slurry under vigorous mixing.

In 1 L glass beaker in a fume hood, 40 g of oxytetracycline (OTC, Sigma) was added and dissolved in an equal amount of 95% isopropyl alcohol. About two hundred (200) g castor oil (Sigma), 20 g cationic surfactant (Cationic Emulsifier-1, Abitec Corp., Janesville, Wis.) and about 600 g fish oil (available from a local vitamin store) were added and mixed together to obtain a clear oily solution. The dissolved OTC was then slowly mixed with about 1800 g salmon protein isolate (Marine Bioproducts AS, Norway) until the powder appeared uniformly wet. The OTC coated salmon protein then slowly added to the alginate and chitosan slurry and gently mixed (500-1000 RPM) until smooth slurry was obtained. Alternatively, the salmon protein isolate can be mixed separately in the alginate and chitosan slurry followed by mixing in the oil solubilized OTC.

Pellet formation: The OTC containing slurry was dropped and pellets were form by cross linking in a water bath containing 2% calcium chloride. Pellets were collected and dried at 60° C. in a vacuum oven (Shel Lab, Cornelius, Oreg.). FIG. 2 depicts an image of the bioadhesive pellets of the present invention having adjusted density for marine water. The left picture shows freeze dried pellets and the right picture shows rehydrated pellets sinking in marine water. The composition of the pellets is provided in Table 3. The OTC pellets are useful for treating a broad range of bacterial diseases in farmed fish.

TABLE 3

| OTC microparticle composition (g dry weight/100 g) | |
|---|---|
| Alginate | 6 g |
| Chitosan | 3 g |
| Soy lecithin | 3 g |
| Tween-80 | 3 g |
| Propylmatte-31 | 7 g |
| Tricalciumphosphate | 9 g |
| Salmon proteins isolate | 47.5 g |
| Castor oil | 5 g |
| Olive oil | 15 g |
| Cationic emulsifier | 0.5 g |
| Oxytetracycline | 1 g |

Example 4

Production of Bioadhesive Microparticles Containing a Mixture of Biocides for Treating Aquatic Infrastructure Such as Pipes, Pumps, Cables and other Water Submerged Surfaces Heavy sinking bioadhesive microparticles were produced as described in Example-2 with the exception of replacing the PPP with equal amount of TCP and the soy protein isolate with equal amount of unmodified resistant starch (Hylon V, National Starch and Chemical, Bridgewater, N.J.). A broad mixture of biocides are prepared by mixing in a one (1) L glass beaker in a fume hood, 10 g Rotenone, 10 g piperonyl butoxide (PBO) and 10 g antimycin A (all from Sigma) and dissolving them in an equal amount of chloroform. About two hundred (200) g castor oil (Sigma), 20 g cationic surfactant (Cationic Emulsifier-1, Abitec Corp., Janesville, Wis.) and about 200 g coco-butter (available from a local store) are added and mixed together in a water bath at 40° C. to obtain a clear oily solution. The beaker containing the dissolved biocides was kept in 40° C. water bath in the hood and under a stream of nitrogen for about two (2) hours to allow the chloroform to evaporate. The dissolved biocides were then slowly mixed with about 1880 g resistant starch until the powder appeared uniformly wet. The biocides coated starch granules are then slowly added to the chitosan solution and gently mixed (500-1000 RPM) until a smooth slurry is obtained. The solution is spray dried using 30" spray dryer (S/S Mobile Minor, GEA Process Engineering Inc., Columbia, Md.). The dry micro particles, mostly in a size range from 5 microns to 20, microns were collected and stored for later use. The heavy sinking microparticles are useful for treating water-submerged surfaces such as pipes, pumps, cables and other submerged structures against bottom feeder invasive organisms such as mussels and clams.

Example 5

Production of Bioadhesive Microparticles Containing Niclosamide for Treating Aquatic Invasive Invertebrates A 20 L Alginate and chitosan solution is prepared as described in Example 1, using a 1:3 mixture of TCP/PPP that provides slow sinking microparticles. In a one (1) L glass beaker in a fume hood, 40 g of niclosamide (Sigma) is added and dissolved in an equal amount of acetone. About two hundred (200) g castor oil (Sigma), 20 g cationic surfactant (Cationic Emulsifier-1, Abitec Corp., Janesville, Wis.) and about 200 g coco butter (available from a local vitamin store) are added and mixed in a water bath at 40° C. to obtain a clear oily solution. The warm oily solution is slowly mixed with about 1800 g resistant starch at 40° C. until the powder appeared uniformly wet and then the mixture is cooled down to room temperature while mixing is continued. The powder is kept in the hood and under a stream of nitrogen for about two (2) hours to allow the acetone to evaporate. The dissolved niclosamide is then slowly added to the alginate/chitosan solution and gently mixed (500-1000 RPM) until a smooth and uniform slurry is obtained.

To form fine several microns size droplets, the slurry is slowly added to another mixing vessel containing 50 L cold liquid paraffin or chloroform under vigorous homogenizing at 10,000 RPM. The emulsion is kept cold at below 10° C. to minimize potential leaching and loss of niclosamide into the liquid paraffin. Two (2) L cold solution of 10% calcium chloride is slowly added to the emulsion under gentle mixing of about 500-1000 RPM and the preformed droplets allowed to cross-linked and harden for about 30 min. The mixture is then allowed to settle and the paraffin is discharged from the vessel. The wet intact niclosamide microparticles mostly in a size range between 4 microns and 12 microns are stored for later use. Alternatively, the alginate/chitosan slurry containing the oil-dissolved niclosamide is extruded into cold (about 10° C.) water bath containing 2% calcium chloride and the cross-linked harden gel strings are harvested and dried in a convection oven, vacuum oven or freeze dryer and the like. The dried strings are then finely milled to a particle size below 10 microns. The slow sinking microparticles are useful against invasion of an invertebrate organism such as sea snail and sea lamprey.

Example 6

Figure 3:
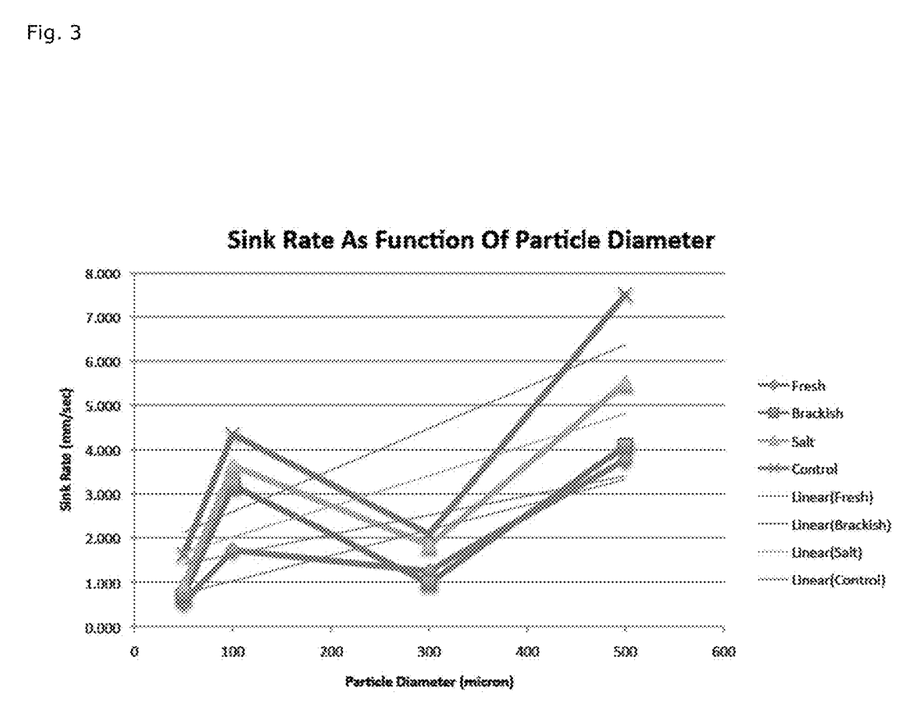

Density Adjustment of the Microparticles for Application in Water Bodies having Various Salinities Microparticles having various densities and size range were produced according to Example 1. The sink rate of the particles as a function of their size and water density is presented in FIG. 3. Low density microparticles (having low TCP/PPP ratio) at an average particle size of about 100 micron remain in the upper one (1) meter depth of fresh water body for about 30 minutes and for about one (1) hour in marine water body.

Example 7

Figure 4:
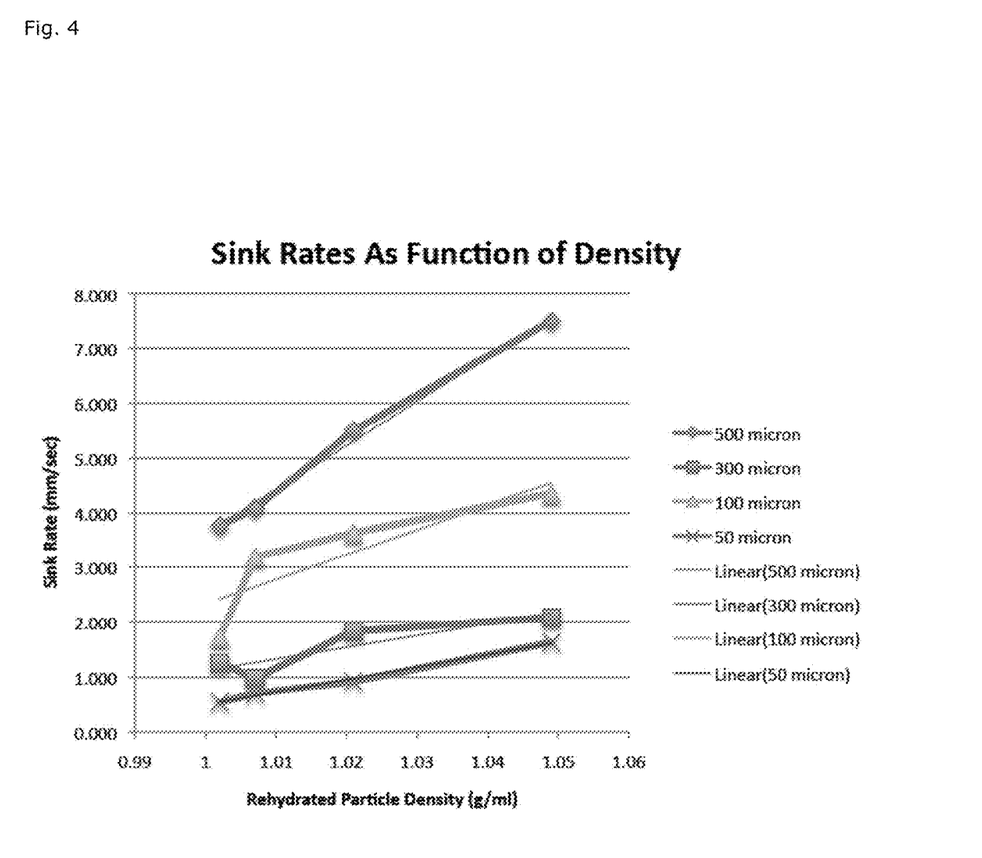
Figure 5:
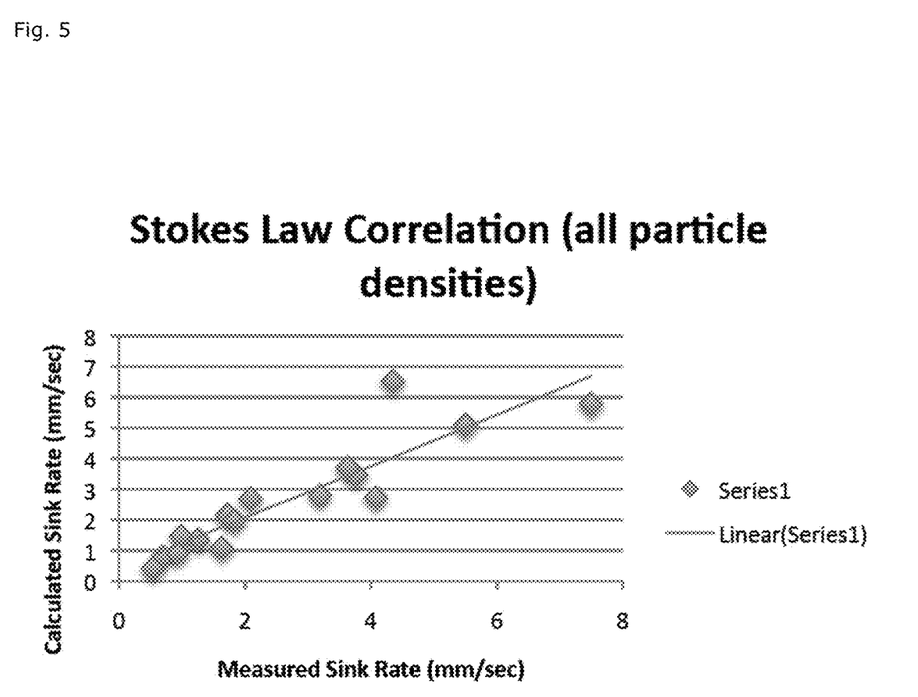

Sink Rate Adjustment of the Microparticles for Application in a Desired Water Body Microparticles having various densities and size ranges were produced according to Example 1. The sinking rate of the particles as a function of their size and density in fresh water body is presented in FIG. 4. It has been demonstrated that by varying the TCP/TPP ratio, according to the claims of the present invention, the presence of 100 microns microparticles in the upper one (1) meter depth of fresh water bodies is extended from about 30 minutes to about one (1) hour. FIG. 5 demonstrates that the sinking rate of the microparticles in a given water body obeys Stokes law, thus allowing for the design of such microparticles having a desirable sinking rate to target a specific organism in the water body.

Example 8

Retention of Biocide Activity within the Composition during Exposure in Water

Microparticles containing 10% dry weight olive oil were produced according to Example 1. The dry microparticles are placed in warm fresh water (40° C.) and the amount of oil leaching into the water was measured over a time period of six (6) hours. Results showed that over 80% of the oil remained within the microparticles even after 6 hours exposure to in warm water. This example demonstrates the capacity of the microparticles to retain commonly used biocides, which are mostly water insoluble, and prevent their exposure to non-targeted native organisms. While utilizing other functionalities of the microparticles such as size, sink rate and nutritional attraction to selectively target only the unwanted organism.

Example 9

Bio-adhesive Properties of the Composition

Bio-adhesive microparticles excluding the bioactive and with or without chitosan are produced as described in Example 2. The bioadhesive property of the microparticles is tested by adhering them with bacterial culture of *Lactobacillus rhamnosus* sp. Five hundred (500) mg of dry microparticles in a size range between 100 microns and 150 microns are placed on a small 50 micron mesh sieve. The particles are gently washed with 100 ml of sterile PBS buffer followed by 100 ml of live bacterial culture containing 10E8 CFU/ml in PBS buffer. The microparticles then washed with 100 ml of sterile PBS buffer and transferred to a beaker containing 100 ml sterile PBS buffer added with 1% Tween-80. The microparticle solution is homogenized at 10,000 RPM using a lab homogenizer and was serially diluted before plating on LMRS agar plates. The colony forming units (CFU) are recorded after 72 h incubation at 37° C. and calculated per mg dry weight particles. Results are presented in Table 4.

TABLE 4

Bio-adhesive properties of the microparticle

| Microparticles without chitosan | 10E2 CFU/mg dry weight |
| Microparticles with chitosan | 10E4 CFU/mg dry weight |

This example shows the bioadhesive property of microparticle due to the incorporation of bioadhesive polymer such as chitosan within the alginate matrix. Thus, the microparticles can be administered as a bio-adhesive device that adheres to mucosal tissue of the aquatic organism (e.g. gill, skin, oral cavity and along the digestive system) for absorption of the biocidal active agent(s) through the organism mucosal tissue.

Example 10

Controlling the Over-growth of an Invasive Organism Such as Asian Carp with Rotenone/PBO Microparticles Dry microparticles containing a 1:1 mixture of Rotenone and PBO are produced according to Example 1. An open water body located in a recreational river and which is overpopulated with Asian carp is dosed with a quantity of the dry particles, so as to achieve a concentration of 50 ppm as active biocides in the upper one (1) meter depth of the water body. Biocide measurement shows Rotenone concentrations well above 20 ppm for several hours, suggesting that most of the particles remain buoyant in the water body, which allows for effective exposure of the biocide to a large number of fish. Massive mortality and morbid fish is observed the day following the treatment. Biocide measurement after 24 hours shows Rotenone concentrations below 2 ppm, indicating that most of the particles disappeared from the upper 1 meter depth water body and were either consumed by the fish or sunk to the bottom of the water column where natural biodegradation of the particles can take place. Substantial cost savings are achieved due to the more efficient and selective application of the biocide microparticles.

Example 11

Treating Sick Trout Fish with OTC Microparticles

Trout broodstock are stocked at 10 kg per $m^3$ of fresh water and at temperature of 10° C. Water quality is maintained by rapidly exchanging the tank water through mechanical and biofiltration systems. Fish are fed 4 times daily a total ration of 1% body weight on a commercial feed and 0.5% (wet weight) microparticles as described in Example 3 for 7 days. Blood samples were taken for OTC profile analysis and compared with fish fed only standard commercial feed containing 0.5% OTC. Results show that fish more efficiently absorb OTC from the microparticles of the present invention than from the OTC containing feed.

Example 12

Pigmenting Salmon Flesh with Astaxanthin Pellets

Atlantic salmon fish are raised in open sea cages. Thirty (30) days before harvest, the fish are fed 20% of their daily a total ration of 1% body weight on astaxanthin containing pellets as described in Example 3. Blood samples and flesh color are analyzed for astaxanthin content and compared with fish fed standard commercial feed containing astaxanthin. Results show that fish more efficiently absorb astaxanthin from the pellets of the present invention than from the commercial astaxanthin containing feed.

REFERENCES

The contents of all references cited herein are hereby incorporated by reference herein for all purposes.

U.S. Patent Documents

| | | |
|---|---|---|
| 6,194,194 | Molloy, Daniel | Feb. 27, 2001 |
| 3,851,053 | Cardarlleri, et al. | Nov. 01, 1971 |
| 4,400,374 | Cardarlleri, et al. | Jul. 24, 1980 |
| 3,059,379 | Attoe, Osborne J. | Oct. 23, 1962 |
| 4,428,457 | Fikkers, et al. | Sep. 24, 1982 |
| 4,019,890 | Fujita, et al. | Dec. 03, 1974 |
| 2,891,355 | Nelson, Florian N. | Jun. 23, 1959 |
| 3,336,155 | Rowe, Englebert L. | Aug. 15, 1967 |
| 3,276,857 | Stansbury, et al. | Oct. 04, 1966 |
| 4,239,754 | Sache, et al. | Oct. 25, 1977 |

OTHER REFERENCES

[1-13]

1. Mack, R. N., D. Simberloff, W. M. Lonsdale, H. Evans, M. Clout, and F. Bazzaz. 2000. Biotic invasions: causes, epidemiology, global consequences, and control. Ecological Applications. 10(3): 689-710.
2. Myers, J. H., Simberloff, D., Kuris, A. M., & Carey, J. R. 2000. Eradication revisited—dealing with non-indigenous species. Trends in Ecology and Evolution, 15, 316-320.
3. Pimentel, D., L. Lach, et al. (2000). “Environmental and economic costs of non-indigenous species in the United States.” Bioscience 50(1): 53-65.
4. Varney, R. W. 2004. Fighting the Spread of Invasive Species in Connecticut/Vermont. U.S. Environmental Protection Agency (EPA). www.epa.gov/libraries/region1
5. Joseph M. Caffrey, Stephanie Evers, Michael Millane and Helen Moran. 2011. Current status of Ireland’s newest invasive species—the Asian clam *Corbicula fluminea* (Müller, 1774). Aquatic Invasions (2011) Volume 6, Issue 3: 291-299.
6. Aldridge D C, Elliott P, Moggridge G D (2006). Microencapsulated BioBullets for the control of biofouling zebra mussels. Environmental Scientific Technology 40: 975-979
7. O’Neill, C. R. and MacNeill, D. B. 1991. The zebra mussel (*Dreissena polymorpha*): an unwelcome north american invader. Coastal Resources Fact Sheet, November 1991, Sea Grant, Cornell Cooperative Extension, State University of New York.
8. Kornis M S, Mercado-Silva N, Vander Zanden M J. 2012. Twenty years of invasion: a review of round goby *Neogobius melanostomus* biology, spread and ecological implications. J Fish Biol. 2012 February; 80(2): 235-85.)
9. Daniel P. Molloy and Denise A. Mayer, Overview of a Novel Green Technology: Biological Control of Zebra and Quagga Mussels with *Pseudomonas fluorescens*, Version 6: Updated Aug. 24, 2007.
10. Claudi and Macke, 1994; Karen Perry J E John Lynn, Detecting physiological and pesticide-induced apoptosis in early developmental stages of invasive bivalves, Hydrobiologia (2009) 628:153-164
11. D. F. Villamar and C. J. Langdon. 1993. Delivery of dietary components to larval shrimp (*Penaeus vannamei*) by means of complex microcapsules. Marine Biology, 115:635.
12. D. Siebers and A. Winkler. 1984. Amino-acid uptake by mussels, *Mytilus edulis*, from natural seawater in a flow-through system. Helgoland Marine Search. Vol. 38, 189-199
13. D.C. Sigee (Ed). Freshwater microbiology: biodiversity and dynamic interactions of Microorganisms in the Aquatic Environment. John Wiley and Sons, 2005-524 pages)

We claim:

1. Particles for delivering a bioactive agent, each of said particles comprising a polymer matrix, droplets of an oil with at least one bioactive agent dissolved or dispersed therein, at least first and second density-adjusting compounds and at least one nutrient, wherein the first density-adjusting compound is polypropylene wax having a density lower than 1 g/cm$^3$, and the second density-adjusting compound has a density greater than 1 g/cm$^3$ and is tricalcium phosphate;
wherein the polymer matrix comprises at least one bioadhesive polymer and wherein the droplets with the at least one bioactive agent dissolved or dispersed therein are embedded in the polymer matrix;
wherein the bioactive agent is approximately 0.05% to 10% by weight, the bioadhesive polymer is approximately 0.05% to 10% by weight, the first and second density-adjusting compounds together are approximately 0.05% to 30% by weight and the nutrient is approximately 0.05% to 50% by weight of the particles.

2. The particles according to claim 1, wherein the bioactive agent is chosen from biocides, therapeutic substances, nutraceutical substances and mixtures thereof and wherein the bioactive agent is dissolved or dispersed in a mixture of oil and cationic surfactant.

3. The particles according to claim 1, wherein the bioactive agent is a biocide chosen from the group consisting of Antimycin A, Piperonyl Butoxide (PBO), Pyrethrins, Rotenone and Cube Resins other than Rotenone, Niclosamide, the aminoethanol salt of Niclosamide, Trifluoromethyl-4-nitrophenol (TFM) and mixtures thereof.

4. The particles according to claim 1, wherein the bioactive agent is a therapeutic substance chosen from the group consisting of antibiotics, antibacterials, antivirals, antifungals, antiprotozoals, antiparasitics and mixtures thereof.

5. The particles according to claim 1, wherein the bioactive agent comprises one or more antibiotics.

6. The particles according to claim 1, wherein the bioactive agent is a nutraceutical agent chosen from the group consisting of proteins, peptides, fatty acids, amino acids, vitamins, carotenes, hormones and mixtures thereof.

7. The particles according to claim 1, wherein the bioadhesive polymer is chosen from the group consisting of cationic hydroxyethyl cellulose and cationic hydrophobically modified hydroxyethyl cellulose, polyethyleneimine, diethylaminoethyl-dextran, poly-L-lysine, chitosan, modified chitosans, cationic guar and mixtures thereof.

8. The particles according to claim 1, wherein the nutrient is selected from the group consisting of animal or plant meals, proteins, fish protein isolate, soy protein isolate, pea protein isolate, canola protein isolate, peptides, amino acids, fatty acids, starches and mixtures thereof.

9. The particles according to claim 1, wherein the bioactive agent is water—insoluble, the oil is selected from the group consisting of fish oil, rapeseed oil, sunflower oil, soy oil, olive oil, cocoa butter, coconut oil, palm oil, castor oil and combinations thereof, and the droplets of oil further comprise a cationic surfactant.

10. The particles according to claim 1, wherein the bioadhesive polymer in the matrix is mixed with a matrix-forming polymer selected from the group consisting of ethyl-, methyl- and carboxymethyl-cellulose, agar, carrageenan, alginate, pectin, gelatin, and glutens.

11. The particles according to claim 1, wherein the particles remain intact and retain the bioactive agent for at least two (2) hours if placed in water.

12. The particles according to claim 1, wherein the particles have dimensions of approximately 5-50 microns.

13. The particles according to claim 1, wherein the particles have dimensions of approximately 50-1000 microns.

14. The particles according to claim 1, wherein the particles have dimensions of approximately 1000-10,000 microns.

15. A method of producing the particles according to claim 1, comprising steps of: (i) Preparing a bioadhesive polymer solution; (ii) Forming a polymer slurry by emulsifying into the bioadhesive polymer solution at least first and second density-adjusting compounds in amounts adapted to provide a predetermined desired particle density according to Stokes Law; (iii) Dissolving or dispersing a bioactive agent into a mixture of an oil and a cationic surfactant; (iv) Providing a nutrient; (v) Mixing the nutrient and the product of step (iii), either separately or simultaneously as the product of step (iii) coated onto the nutrient, into the polymer slurry; (vi) Granulating or atomizing the product of step (v) into particles having a desirable size and dimension; and (vii) Hardening the particles through a physical or chemical reaction.

16. The method according to claim 15, wherein the bioadhesive polymer solution comprises a mixture of alginate and chitosan.

17. The method according to claim 15, wherein the oil-dissolved or dispersed bioactive agent and the nutrient are added separately into the polymer slurry.

18. The method according to claim 15, wherein step (vii) comprises air drying or cooling.

19. The method according to claim 15, wherein step (vii) comprises chemical reaction.

20. The method according to claim 15, wherein steps (vi) and (vii) comprise dropping or atomizing the product of step (v) into a water bath containing multivalent cations or having a pH that causes hardening.

21. A method of controlling invasive organisms in an aquatic ecosystem, comprising dispersing, into a water body requiring treatment, the particles according to claim 1, wherein the particles each comprise: (i) Approximately 0.05% to 10% by weight of at least one bioactive agent selected from the group consisting of Antimycin A, Piperonyl Butoxide (PBO), Pyrethrins, Rotenone and Cube Resins other than Rotenone, Niclosamide, the aminoethanol salt of Niclosamide, trifluoromethyl-4-nitrophenol (TFM) and mixtures thereof, wherein the at least one bioactive agent is dissolved or dispersed in droplets of an oil; (ii) A matrix comprising at least one bioadhesive polymer selected from the group consisting of cationic hydroxyethyl cellulose and cationic hydrophobically modified hydroxyethyl cellulose, polyethyleneimine, diethylaminoethyl-dextran, poly-L-lysine, chitosan, modified chitosans, cationic guar and mixtures thereof, wherein the at least one bioadhesive polymer constitutes approximately 0.05% to 10% by weight of the particles and wherein the droplets of oil are embedded in the matrix; (iii) Approximately 0.05% to 30% by weight in total of said at least first and second density-adjusting compounds; and (iv) Approximately 0.05% to 70% by weight of at least one nutrient selected from the group consisting of animal or plant proteins, peptides, amino acids, fatty acids, starches and mixtures thereof.

22. The method as recited in claim 21, wherein the matrix further comprises a matrix-forming polymer mixed therein.

23. The method as recited in claim 21, wherein the particles are microparticles prepared by a process comprising atomizing a slurry to form microdroplets and hardening the microdroplets through a physical or chemical reaction.

24. The method as recited in claim 21, wherein the particles are pelleted particles prepared by a process comprising pelleting the slurry and hardening the pellets through a physical or chemical reaction.

25. The method as recited in claim 21, wherein the particles are dry.

26. The particles according to claim 1, wherein the particles further comprise lecithin.

27. Particles made by the method of claim 15.

28. The particles according to claim 1, wherein the bioactive agent is a toxic agent.

29. The method as recited in claim 15, wherein steps (vi) and (vii) comprise atomizing the product of step (v) to form microdroplets and hardening the microdroplets through a physical or chemical reaction, wherein the particles are microparticles.

30. The method as recited in claim 15, wherein steps (vi) and (vii) comprise pelleting the product of step (v) and hardening the pellets through a physical or chemical reaction, wherein the particles are pelleted particles.

* * * * *